(12) United States Patent
Yamasaki et al.

(10) Patent No.: US 10,828,013 B2
(45) Date of Patent: Nov. 10, 2020

(54) PIEZOELECTRIC ELEMENT, ULTRASONIC PROBE, ULTRASONIC MEASUREMENT DEVICE, AND MANUFACTURING METHOD OF PIEZOELECTRIC ELEMENT

(71) Applicant: SEIKO EPSON CORPORATION, Tokyo (JP)

(72) Inventors: Sayaka Yamasaki, Suwa (JP); Hiroaki Tamura, Shimosuwa-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 1045 days.

(21) Appl. No.: 15/340,920

(22) Filed: Nov. 1, 2016

(65) Prior Publication Data

US 2017/0119350 A1    May 4, 2017

(30) Foreign Application Priority Data

Nov. 2, 2015 (JP) ................. 2015-215987

(51) Int. Cl.
*H01L 41/08* (2006.01)
*A61B 8/00* (2006.01)
(Continued)

(52) U.S. Cl.
CPC .......... *A61B 8/4494* (2013.01); *A61B 8/4444* (2013.01); *B06B 1/06* (2013.01); *B06B 1/0607* (2013.01); *G01P 15/09* (2013.01); *G01P 15/0922* (2013.01); *H01L 41/04* (2013.01); *H01L 41/081* (2013.01); *H01L 41/083* (2013.01); *H01L 41/0825* (2013.01); *H01L 41/1136* (2013.01); *H01L 41/1876* (2013.01);
(Continued)

(58) Field of Classification Search
CPC ......... B06B 1/06; B06B 1/0607; H01L 41/04; H01L 41/0825; H01L 41/083
See application file for complete search history.

(56) References Cited

U.S. PATENT DOCUMENTS

2004/0140865 A1* 7/2004 Komuro ............... H03H 3/04
   333/133
2008/0252178 A1* 10/2008 Yamada ............. H03H 9/02023
   310/361

(Continued)

FOREIGN PATENT DOCUMENTS

JP    60-206315 A    10/1985
JP    61-220596 A    9/1986
JP    2008-173177 A    7/2008

*Primary Examiner* — Bryan P Gordon
(74) *Attorney, Agent, or Firm* — Chip Law Group (57) ABSTRACT

A piezoelectric element includes: a piezoelectric body; and a vibrating plate including single crystal silicon having anisotropy having orientation with a relatively high Poisson's ratio and orientation with a relatively low Poisson's ratio (hereinafter, referred to as "low Poisson's ratio orientation") as a vibrating material, in which the piezoelectric body and the vibrating plate are laminated on each other so that the low Poisson's ratio orientation is in a direction along a high expansion and contraction direction among a direction where a degree of expansion and contraction caused according to a support structure of the piezoelectric body is relatively high (hereinafter, referred to as "high expansion and contraction direction") and a direction where a degree thereof is relatively low.

19 Claims, 10 Drawing Sheets

[ SEC A-A ]

(51) Int. Cl.
*H01L 41/113* (2006.01)
*G01P 15/09* (2006.01)
*H02N 2/18* (2006.01)
*B06B 1/06* (2006.01)
*H01L 41/04* (2006.01)
*H01L 41/083* (2006.01)
*H01L 41/187* (2006.01)
*H01L 41/257* (2013.01)
*H01L 41/29* (2013.01)
*H01L 41/312* (2013.01)

(52) U.S. Cl.
CPC ............ *H01L 41/257* (2013.01); *H01L 41/29* (2013.01); *H01L 41/312* (2013.01); *H02N 2/186* (2013.01)

(56) References Cited

U.S. PATENT DOCUMENTS

2016/0334581 A1* 11/2016 Facer ..................... G02B 6/264
2017/0157931 A1* 6/2017 Murakami .......... H01L 41/0973
2017/0256700 A1* 9/2017 Murakami ............... B41J 2/045

\* cited by examiner

PIEZOELECTRIC ELEMENT, ULTRASONIC PROBE, ULTRASONIC MEASUREMENT DEVICE, AND MANUFACTURING METHOD OF PIEZOELECTRIC ELEMENT

BACKGROUND

1. Technical Field

The present invention relates to a piezoelectric element and the like.

2. Related Art

Biological information is measured by using an ultrasonic probe and an ultrasonic measurement device using a piezoelectric element as a transducer for ultrasonic transmitting and receiving, and vascular functions are evaluated or vascular diseases are determined. For example, JP-A-2008-173177, for example, discloses an ultrasonic probe and an ultrasonic measurement device which automatically detect vascular walls by using reflected wave signal intensity from biological tissues obtained by processing amplitude information of received ultrasonic waves and a moving velocity of biological tissues obtained by processing phase information of received ultrasonic waves.

A piezoelectric element used in the ultrasonic probe and the ultrasonic measurement device is prepared by laminating a piezoelectric body on a vibrating plate on a thin film, as disclosed in JP-A-60-206315, for example.

When the attention is paid on reception sensitivity of a piezoelectric element, it is important to increase electric charges generated when receiving ultrasonic waves. The vibrating plate is set to be thin as one method thereof, but there is limitation on the thinning of the vibrating plate due to a restriction of a manufacturing technology and the improving measures of sensitivity by decreasing a thickness of the vibrating plate has reached its limit.

SUMMARY

An advantage of some aspects of the invention is to provide a new technology of improving reception sensitivity of a piezoelectric element which is different from the decreasing of a thickness of a vibrating plate.

A first aspect of the invention is directed to a piezoelectric element including: a piezoelectric body; and a vibrating plate including single crystal silicon having anisotropy having orientation with a relatively high Poisson's ratio and orientation with a relatively low Poisson's ratio (hereinafter, referred to as "low Poisson's ratio orientation") as a vibrating material, in which the piezoelectric body and the vibrating plate are laminated on each other so that the low Poisson's ratio orientation is in a direction along a high expansion and contraction direction among a direction where a degree of expansion and contraction caused according to a support structure of the piezoelectric body is relatively high (hereinafter, referred to as "high expansion and contraction direction") and a direction where a degree thereof is relatively low.

The vibrating plate prepared so that the low Poisson's ratio orientation of the vibrating plate is along the high expansion and contraction direction of the piezoelectric body, is in a so-called taut state, compared to a vibrating plate prepared along other directions, and responsiveness to ultrasonic waves is improved. Therefore, according to the first aspect of the invention, it is possible to prepare a piezoelectric element having high reception sensitivity, even with the same thickness of the material to be cut out for a vibrating plate.

More specifically, as a second aspect of the invention, the piezoelectric element according to the first aspect of the invention may be configured such that plane orientation of the single crystal silicon is [001] and the low Poisson's ratio orientation is [−110] or [110].

As a third aspect of the invention, the piezoelectric element according to the first aspect of the invention may be configured such that plane orientation of the single crystal silicon is [010] and the low Poisson's ratio orientation is [101] or [10−1].

As a fourth aspect of the invention, the piezoelectric element according to the first aspect of the invention may be configured such that plane orientation of the single crystal silicon is [100] and the low Poisson's ratio orientation is [011] or [01−1].

As a fifth aspect of the invention, the piezoelectric element according to the first aspect of the invention may be configured such that plane orientation of the single crystal silicon is [110] and the low Poisson's ratio orientation is any one of [1−11], [1−12], [−112], and [−111].

As a sixth aspect of the invention, the piezoelectric element according to the first aspect of the invention may be configured such that plane orientation of the single crystal silicon is [011] and the low Poisson's ratio orientation is any one of [11−1], [21−1], [2−11], and [1−11].

As a seventh aspect of the invention the piezoelectric element according to the first aspect of the invention may be configured such that plane orientation of the single crystal silicon is [101] and the low Poisson's ratio orientation is any one of [−111], [−121], [12−1], and [11−1].

An eighth aspect of the invention is directed to an ultrasonic probe including the piezoelectric element according to any one of the first to seventh aspects for reception of ultrasonic waves.

According to the eighth aspect of the invention, it is possible to realize an ultrasonic probe having higher reception sensitivity.

A ninth aspect of the invention is directed to an ultrasonic measurement device including the ultrasonic probe according to the eighth aspect.

According to the ninth aspect of the invention, it is possible to realize an ultrasonic measurement device having higher reception sensitivity.

A tenth aspect of the invention is directed to a manufacturing method of a piezoelectric element including: cutting out a vibrating material to be used in a vibrating plate from a single crystal silicon wafer having anisotropy having orientation with a relatively high Poisson's ratio and orientation with a relatively low Poisson's ratio (hereinafter, referred to as "low Poisson's ratio orientation"); and laminating a piezoelectric body and the vibrating plate so that the low Poisson's ratio orientation is in a direction along a high expansion and contraction direction among a direction where a degree of expansion and contraction caused according to a support structure of the piezoelectric body is relatively high (hereinafter, referred to as "high expansion and contraction direction") and a direction where a degree thereof is relatively low.

According to the tenth aspect of the invention, it is possible to manufacture a piezoelectric element having operation effects of the first aspect of the invention.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Figure 1:
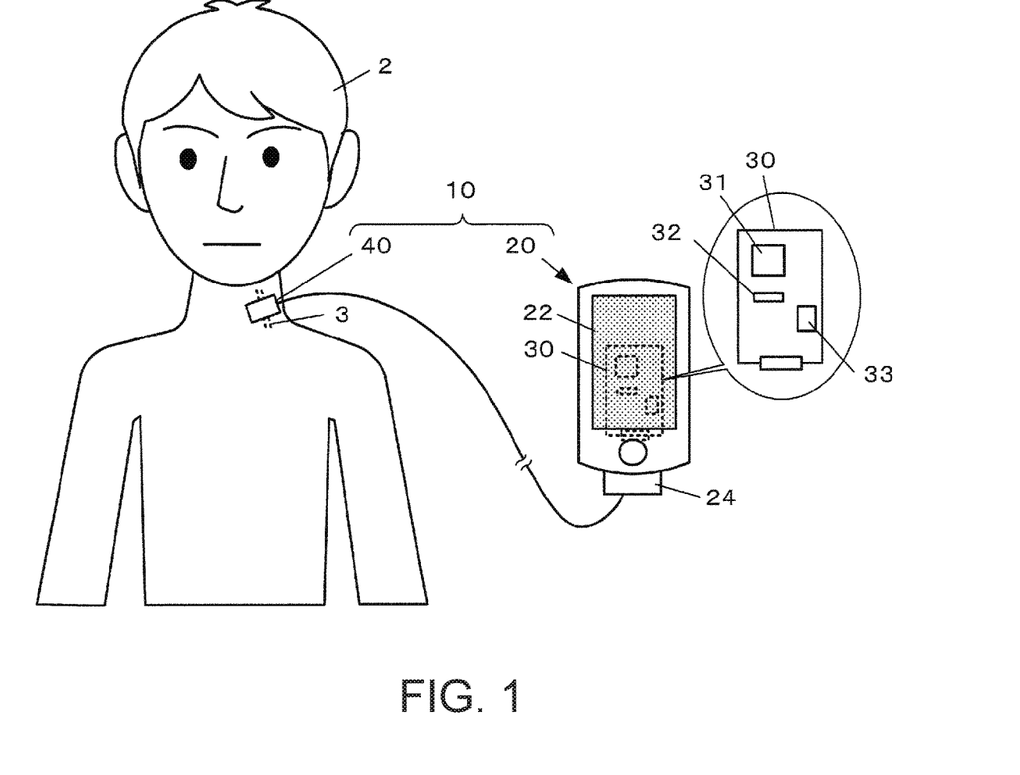
FIG. 1 is a view showing a system configuration example of an ultrasonic measurement device of a first embodiment.

FIG. 1 is a view showing a system configuration example of an ultrasonic measurement device 10 of an embodiment.

The ultrasonic measurement device 10 is a device which measures biological information of a subject 2 by transmitting ultrasonic waves to the subject 2 and measuring reflected waves. In the embodiment, vascular function information such as intima media thickness (IMT) of the carotid 3 is measured as one of the biological information items. In addition to the IMT, other vascular function information or biological information may be measured by estimating a blood vessel diameter or blood pressure from a blood vessel diameter or calculating a pulse from a change of a blood vessel diameter. A measurement target is not limited to a human.

The ultrasonic measurement device 10 includes a measurement control device 20 and an attaching-type ultrasonic probe 40.

The measurement control device 20 is a portable computer and includes a touch panel 22 which serves as both a unit for displaying an image of a measurement result or an operation information and a unit for inputting an operation, an interface circuit 24 which controls transmission and reception of a signal to and from the ultrasonic probe 40, and a control substrate 30. In addition, an embedded battery (not shown) or the like is suitably provided.

A central processing unit (CPU) 31, an IC memory 32 in addition to various integrated circuits such as application specific integrated circuit (ASIC) or a field programmable gate array (FPGA), and a communication IC 33 which realizes data communication with an external device (ultrasonic probe 40 in this embodiment) through the interface circuit 24 are mounted on the control substrate 30. The control substrate 30 realizes various functions according to the embodiment such as ultrasonic measurement by executing control programs stored in the IC memory 32 by the CPU 31 or the like.

That is, the ultrasonic measurement device 10 transmits and emits ultrasonic beams towards biological tissues from the ultrasonic probe 40 attached to the subject 2 and receives reflected waves, due to operation processes of the control substrate 30. It is possible to generate reflected wave data according to biological structures of the subject 2 by amplifying and processing received signals of the reflected waves. The continuous measurement and the data storage of various biological information items are realized based on the reflected wave data.

Figure 2:
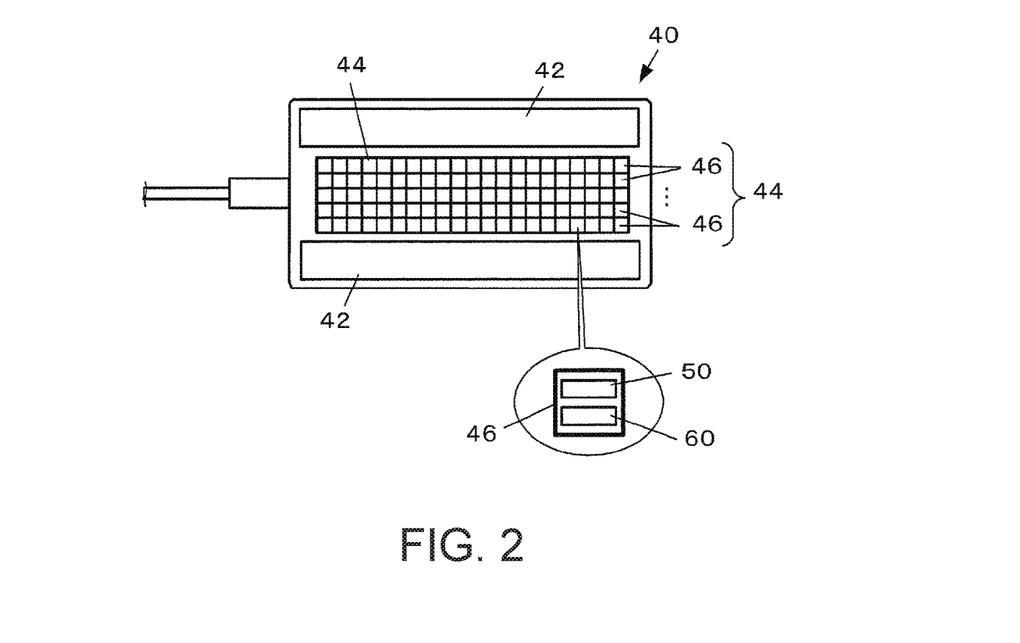
FIG. 2 is a view showing a configuration example of an ultrasonic probe of the first embodiment.

FIG. 2 is a view showing a configuration example of the ultrasonic probe 40 of the embodiment and is a view when seen from a side of the attached surface (ultrasonic transmission and reception surface) of the subject 2.

The ultrasonic probe 40 has a bonding portion 42 which detachably bonds the ultrasonic probe 40 to skin of the subject 2, and an ultrasonic sensor 44 on the attached surface side.

The ultrasonic sensor 44 is an assembly in which a plurality of ultrasonic transducers 46 are two-dimensionally arranged in a long side direction and a short side direction of the ultrasonic transmission and reception surface. The ultrasonic probe 40 is attached to skin surface of the subject 2 in a relative position in which the long side of the ultrasonic sensor 44 crosses over the carotid 3 in a short axis direction.

One ultrasonic transducer 46 includes a first piezoelectric element 50 and a second piezoelectric element 60. The first piezoelectric element 50 transmits the ultrasonic waves and the second piezoelectric element 60 receives the reflected waves.

Figure 3:
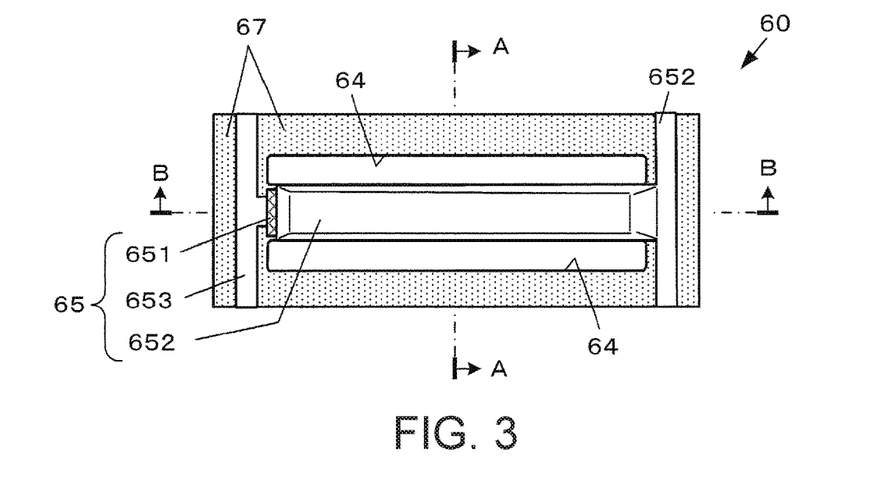
FIG. 3 is a top view showing a configuration example of a second piezoelectric element of the first embodiment.
Figure 4:
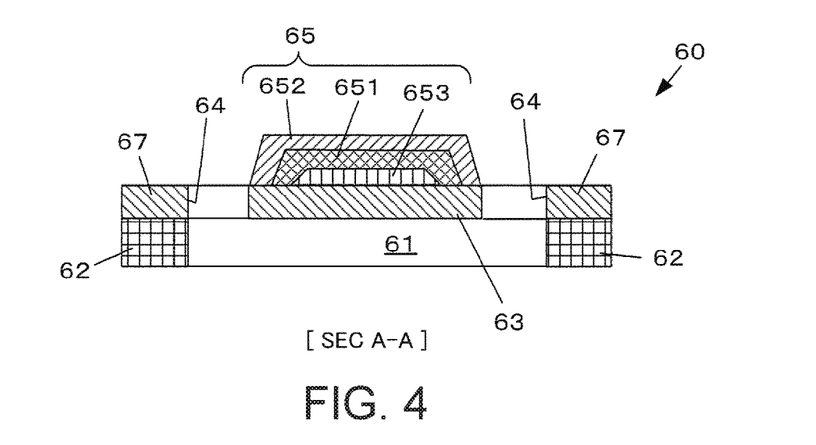
FIG. 4 is a sectional view taken along line A-A of FIG. 3.
Figure 5:
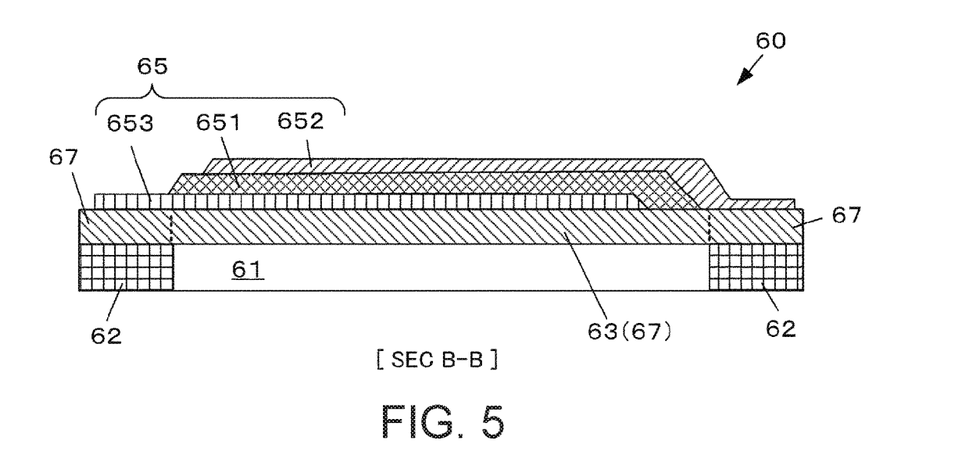
FIG. 5 is a sectional view taken along line B-B of FIG. 3.

FIG. 3 is a top view showing a configuration example of the second piezoelectric element 60 of the embodiment. FIG. 4 is a sectional view taken along line A-A of FIG. 3. FIG. 5 is a sectional view taken along line B-B of FIG. 3.

The second piezoelectric element 60 of the embodiment is an element which generates a voltage in accordance with an external force (ultrasonic waves in a case of this embodiment) received by a piezoelectric body. In the second piezoelectric element 60 of the embodiment, a thin film-shaped silicon layer 67 is bonded to an upper surface of a support substrate 62 which has a rectangular shape in a top view and where a hollow portion 61 is provided (hollow portion 61 is opened). In addition, the hollow portion 61 may be formed after forming the silicon layer 67 on the upper surface of the support substrate 62.

The silicon layer 67 includes a vibrating plate 63 having a both-ends supported beam structure (both-ends fixed support structure) which crosses the hollow portion 61. That is, the silicon layer 67 is bonded so as to cover the hollow portion 61, and two slits 64 are provided along an edge portion of the hollow portion 61 having a rectangular shape in a top view in the longitudinal direction. These two slits 64 precisely realize a bridge structure of a thin plate, that is, both-ends beams of a thin film which crosses the hollow portion 61 in the longitudinal direction. This becomes the vibrating plate 63 which vibrates by receiving ultrasonic waves input from the upper side (front side of FIG. 3 and upper side of FIG. 4 and FIG. 5) or the lower side (rear surface side of FIG. 3 and lower side of FIG. 4 and FIG. 5) of the second piezoelectric element 60.

A power generation element unit 65 is laminated on the upper surface of the vibrating plate 63.

The power generation element unit 65 of the embodiment is configured by interposing a piezoelectric body 651 which is a main element causing piezoelectric effects between an upper electrode 652 and a lower electrode 653. In the embodiment, as the piezoelectric body 651, piezoelectric ceramic or lead zirconate titanate (PZT) is used, but other piezoelectric materials can be suitably selected.

The ultrasonic waves generated from the first piezoelectric element 50 are reflected in the body of the subject 2. The second piezoelectric element 60 receives the reflected waves. When the reflected waves are received, the power generation element unit 65 and the vibrating plate 63 integrally formed are warped, charges according to the warped amount are generated in the piezoelectric body 651, a voltage is generated between the upper electrode 652 and the lower electrode 653. The ultrasonic measurement device 10 calculates the biological information by performing the operation process of the voltage by the measurement control device 20.

A degree of the reception sensitivity of the power generation element unit 65 is dependent on the thin thickness of the vibrating plate 63, but there is a limitation due to a restriction of the manufacturing technology.

Therefore, in the embodiment, a material having anisotropy having different Poisson's ratios due to orientation is used as a thin film material for preparing the vibrating plate 63, in order to increase reception sensitivity of the power generation element unit 65. The second piezoelectric element 60 is prepared so that a high expansion and contraction direction of the vibrating plate 63 is along the orientation in which the Poisson's ratio is relatively low (low Poisson's ratio orientation). The high expansion and contraction direction of the vibrating plate 63 is determined depending on the support structure of the vibrating plate 63, and in the case of this embodiment, the high expansion and contraction direction thereof is the longitudinal direction, because a structure of supporting the longitudinal shaped piezoelectric body 651 with both ends is used.

Figure 6:
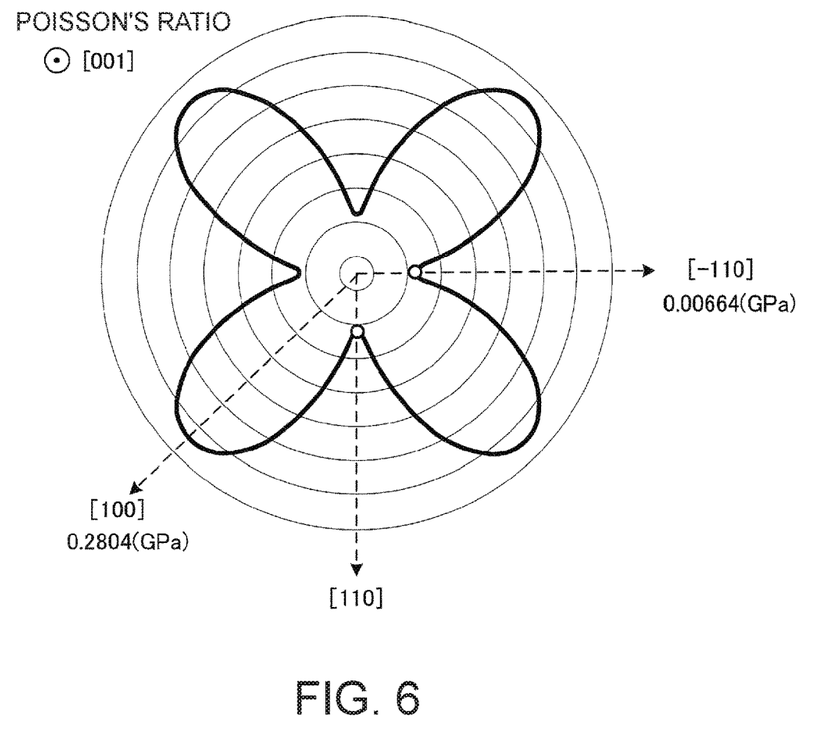
FIG. 6 is a graph showing an example of anisotropy of a Poisson's ratio of the [001] plane of single crystal silicon.

FIG. 6 is a graph showing an example of anisotropy of a Poisson's ratio of the [001] plane of single crystal silicon. A front direction of FIG. 6 is shown as plane orientation [001] and a lower side of FIG. 6 is shown as plane orientation [110].

As shown in FIG. 6, the Poisson's ratio of the [001] plane of the single crystal silicon has anisotropy shown with a four-leaf clover shape. In this embodiment, the material of the vibrating plate 63 is cut out so that the longitudinal direction becomes a direction along any of the plane orientation [110] and the plane orientation [-110] where the Poisson's ratio locally decreases. Since a so-called taut state is obtained in the direction where the Poisson's ratio is low, it is possible to expect expansion and contraction effects in the high expansion and contraction direction of the vibrating plate 63 (in this case, longitudinal direction) and responsiveness to ultrasonic wave reception is improved.

Figure 7:
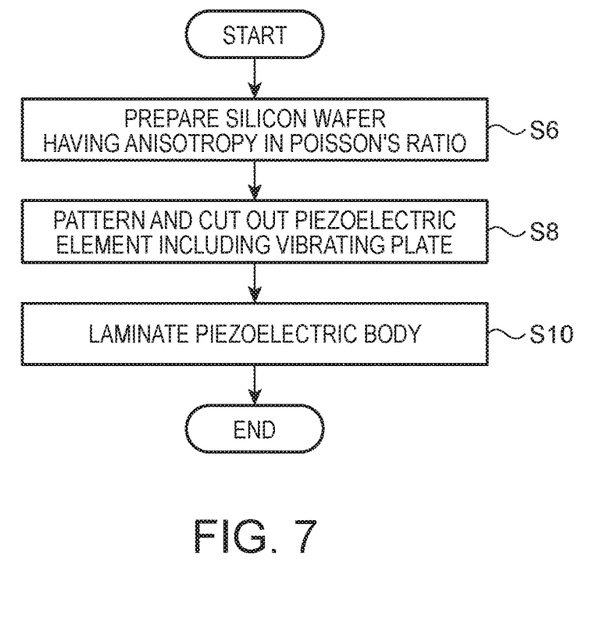
FIG. 7 is a flowchart for illustrating a manufacturing step of the second piezoelectric element of the first embodiment.

FIG. 7 is a flowchart for illustrating a manufacturing step of the second piezoelectric element 60 of the embodiment. First, in the manufacturing step of the second piezoelectric element 60 of the embodiment, a silicon wafer 7 is prepared by slicing a single crystal silicon ingot in the [001] plane orientation where anisotropy of a Poisson's ratio is generated (Step S6). The silicon wafer 7 is not only prepared by slicing the single crystal silicon ingot, but may be prepared by separately purchasing the silicon wafer 7 in the [001] plane orientation.

Next, the second piezoelectric element 60 is patterned to cut out the silicon layer 67 of the second piezoelectric element 60 including a material of the vibrating plate 63, by setting the longitudinal direction of the vibrating plate 63 to be along the low Poisson's ratio orientation in the silicon wafer 7 (Step S8). Then, the second piezoelectric element 60 is prepared by laminating the piezoelectric body 651 including the upper electrode 652 and the lower electrode 653, and the vibrating plate 63 (Step S10).

Figure 8:
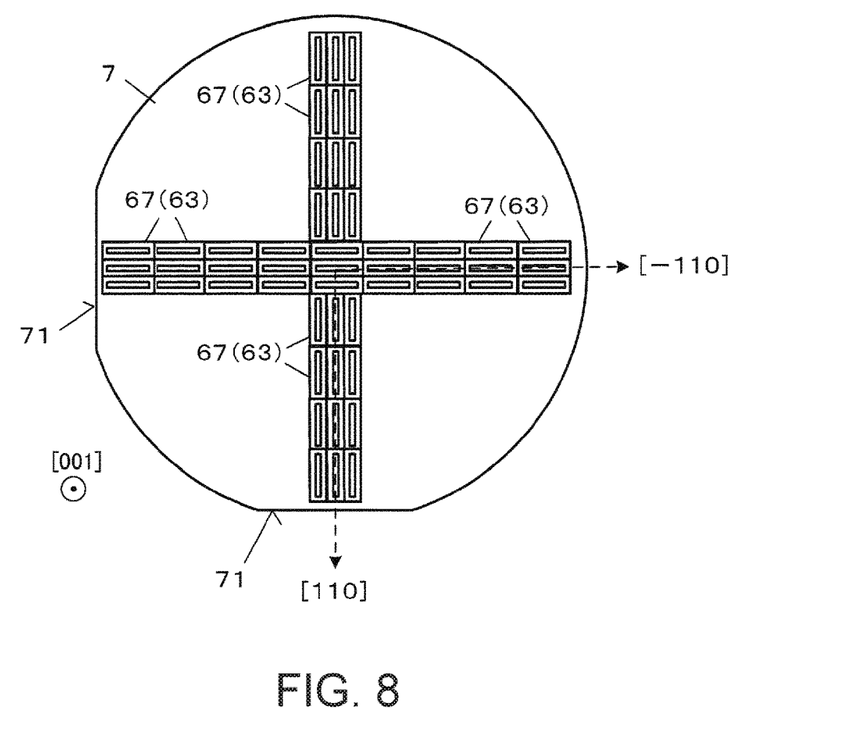
FIG. 8 is a conceptual view for illustrating a positional relationship of patterning of a silicon layer and a vibrating plate of a [001]-orientated silicon wafer of the first embodiment.

FIG. 8 is a conceptual view for illustrating a positional relationship of patterning of the silicon layer 67 including the vibrating plate 63 of the [001]-orientated silicon wafer 7 of the embodiment.

In FIG. 8, an orientation flat 71 is formed on the edge portions corresponding to the plane orientation [110] and the plane orientation [-110] in the [001]-orientated silicon wafer 7. Accordingly, the silicon layer 67 of each second piezoelectric element 60 is patterned by using the orientation flat 71 as a mark. Specifically, the patterning is performed so that the longitudinal direction of the vibrating plate 63 is a direction along any of the plane orientation [110] and the plane orientation [-110] where low Poisson's ratio orientation is obtained.

In FIG. 8, the enlarged size of silicon layer 67 used in each second piezoelectric element 60 than the actual size is shown for convenience of understanding.

Figure 9:
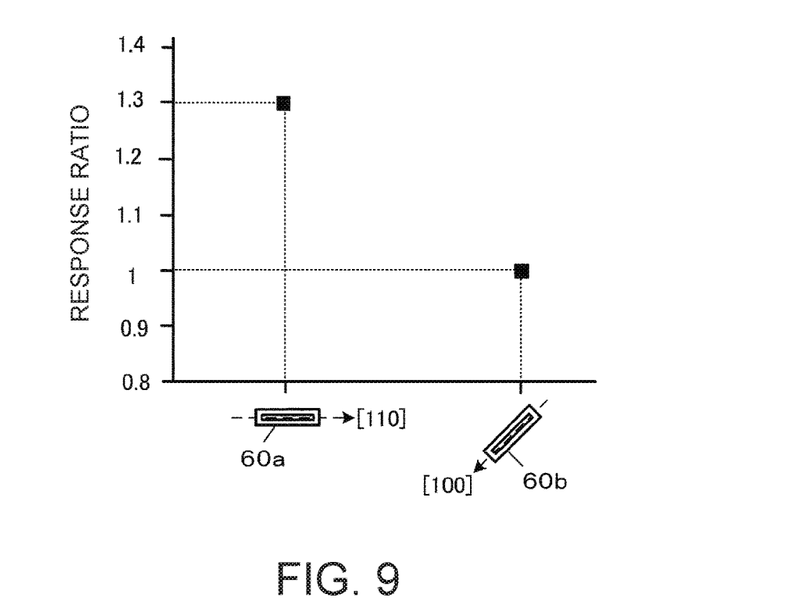
FIG. 9 is a graph of an experiment result showing a difference in sensor sensitivity of 1) a second piezoelectric element prepared by setting a longitudinal direction of the vibrating plate to be along the plane orientation [110] and 2) a second piezoelectric element prepared by setting a longitudinal direction of the vibrating plate to be along the plane orientation [100] from the [001]-oriented silicon wafer.

FIG. 9 is a graph of an experiment result showing a difference in sensor sensitivity of 1) a second piezoelectric element 60a prepared by setting the longitudinal direction of the vibrating plate 63 to be along the plane orientation [110] (low Poisson's ratio orientation) and 2) a second piezoelectric element 60b prepared by setting the longitudinal direction of the vibrating plate 63 to be along the plane orientation [100] (high Poisson's ratio orientation) from the [001]-oriented silicon wafer 7. As shown in FIG. 9, even in a case of the vibrating plate prepared from the silicon wafer 7 having the same thickness, the second piezoelectric element 60a prepared by setting the longitudinal direction to be along the plane orientation [110] (low Poisson's ratio orientation) has responsiveness to ultrasonic waves which is improved 1.3 times of that of the second piezoelectric element 60b prepared by setting the longitudinal direction to be along the plane orientation [100] (high Poisson's ratio orientation).

Hereinabove, according to the embodiment, it is possible to realize a high-sensitivity sensor having improved responsiveness of the second piezoelectric element 60 while maintaining the thickness of the vibrating plate 63.

The laminated structure of the second piezoelectric element 60 of the embodiment is used, but a configuration of further providing a thin film sheet layer on the upper surface side may be used.

Second Embodiment

Next, a second embodiment to which the invention is applied will be described.

This embodiment is basically realized in the same manner as in the first embodiment, but the plane orientation of the silicon wafer used is different and a patterning direction of the silicon layer 67 including the vibrating plate 63 is different. Hereinafter, the differences from the first embodiment will be described and the same reference numerals are used for the same constituent elements and the description thereof will be omitted.

Figure 10:
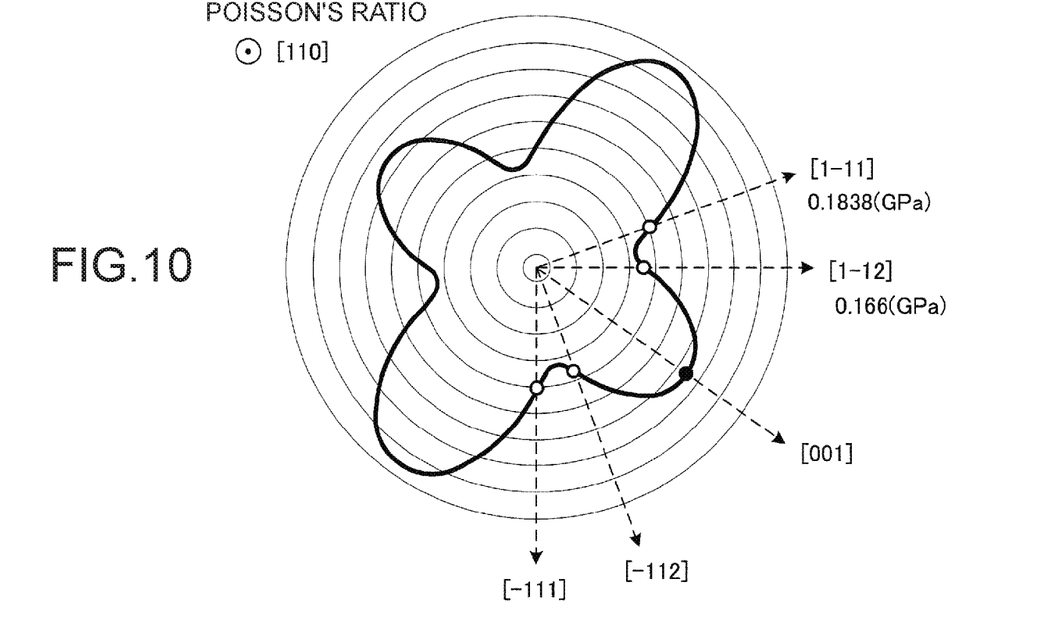
FIG. 10 is a graph showing an example of anisotropy of a Poisson's ratio of the [110] plane of single crystal silicon.

FIG. 10 is a graph showing an example of anisotropy of a Poisson's ratio of the [110] plane of single crystal silicon. A front direction of FIG. 10 is shown as plane orientation [110] and a lower side of FIG. 10 is shown as plane orientation [−111].

As shown in FIG. 10, the Poisson's ratio of the [110] plane of silicon has anisotropy shown with a four-leaf clover shape. Accordingly, in the embodiment, the silicon layer 67 including the vibrating plate 63 is cut out so that the longitudinal direction of the vibrating plate 63 is along any of the plane orientation [−111], the plane orientation [−112], the plane orientation [1−11], and the plane orientation [1−12] where the Poisson's ratio locally decreases.

Figure 11:
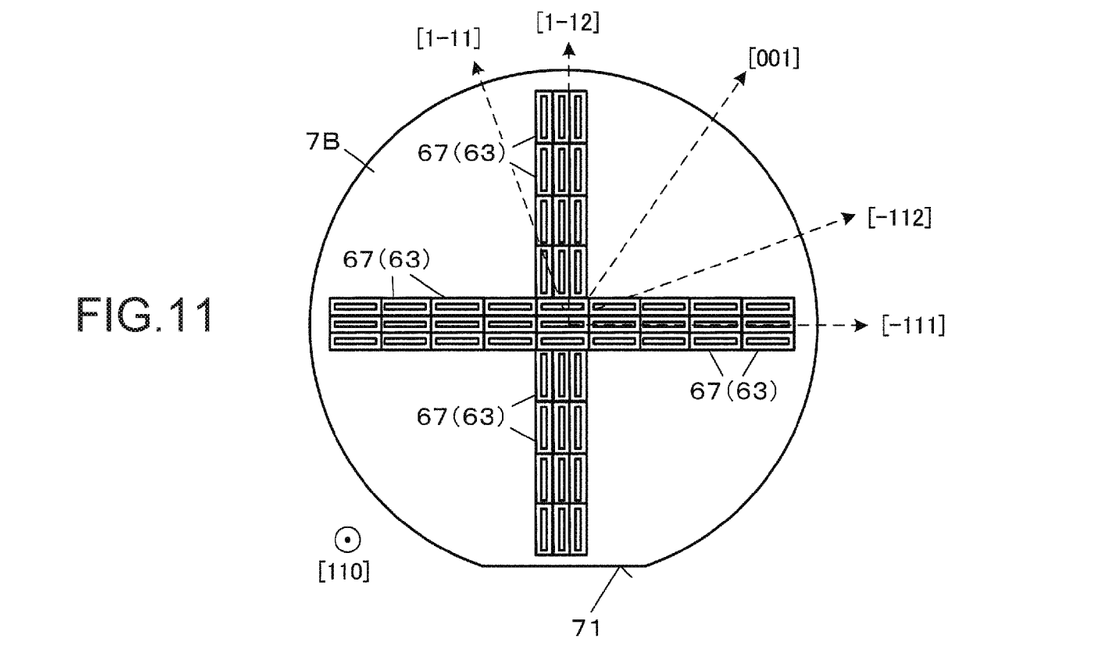
FIG. 11 is a conceptual view for illustrating a positional relationship of patterning of a silicon layer and a vibrating plate of a [110]-orientated silicon wafer of a second embodiment (first example).
Figure 12:
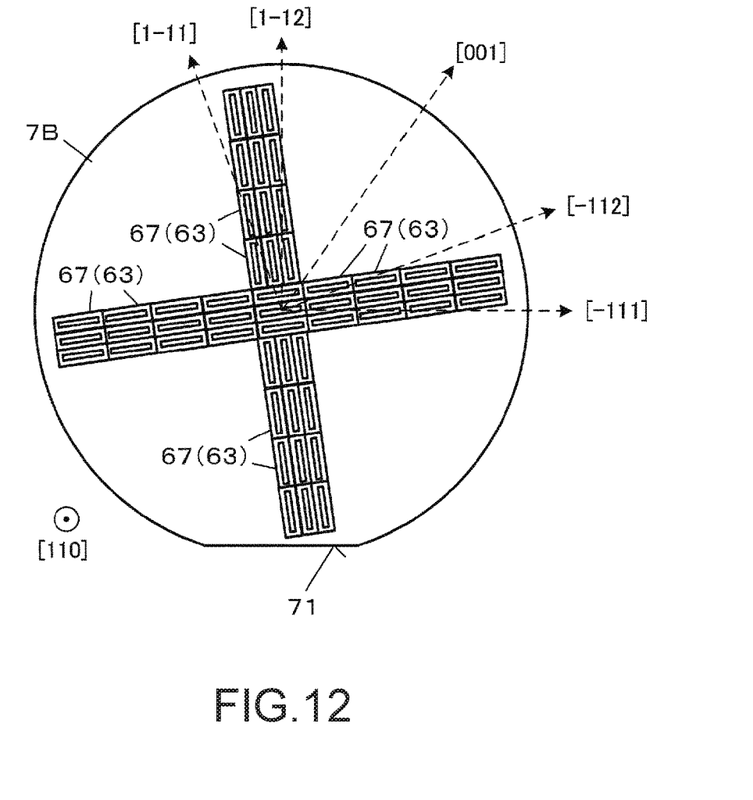
FIG. 12 is a conceptual view for illustrating a positional relationship of patterning of the silicon layer and the vibrating plate of the [110]-orientated silicon wafer of the second embodiment (second example).

FIG. 11 and FIG. 12 are conceptual views for illustrating a positional relationship of patterning of the silicon layer 67 including the vibrating plate 63 of a [110]-orientated silicon wafer 7B.

The orientation flat 71 is formed on the edge portion corresponding to any of the plane orientation [−111], the plane orientation [−112], the plane orientation [1−11], and the plane orientation [1−12] in the [110]-orientated silicon wafer 7B. Accordingly, the silicon layer 67 of each second piezoelectric element 60 is patterned by using the orientation flat 71 as a reference. Specifically, the patterning is performed so that the longitudinal direction of the vibrating plate 63 is a direction along any of the plane orientation [−111], the plane orientation [−112], the plane orientation [1−11], and the plane orientation [1−12] where low Poisson's ratio orientation is obtained.

FIG. 11 shows an example in which the orientation flat 71 is formed on the edge portion corresponding to the plane orientation [1−12] and patterned along the plane orientation [1−12] and the plane orientation [−111]. In FIG. 11, the patterning may be performed along the plane orientation [−112] and the plane orientation [1−11]. Both of the plane orientations are low Poisson's ratio orientations.

In FIG. 10, the low Poisson's ratio orientations are also obtained between the plane orientation [−111] and the plane orientation [−112] and between the plane orientation [1−12] and the plane orientation [1−11]. Therefore, as shown in FIG. 12, the patterning may be performed along the orientation between the plane orientation [−111] and the plane orientation [−112] and orientation between the plane orientation [1−12] and the plane orientation [1−11]. In this case, the longitudinal direction of the vibrating plate 63 becomes a direction along the low Poisson's ratio orientation.

In the second embodiment, it is also possible to realize a high-sensitivity sensor having improved responsiveness of the second piezoelectric element 60 while maintaining the thickness of the vibrating plate 63, in the same manner as in the first embodiment.

Third Embodiment

Next, a third embodiment to which the invention is applied will be described.

This embodiment is basically realized in the same manner as in the first embodiment, but the structure of the second piezoelectric element 60 is different. Hereinafter, the differences from the first embodiment will be mainly described and the same reference numerals are used for the same constituent elements and the description thereof will be omitted.

Figure 13:
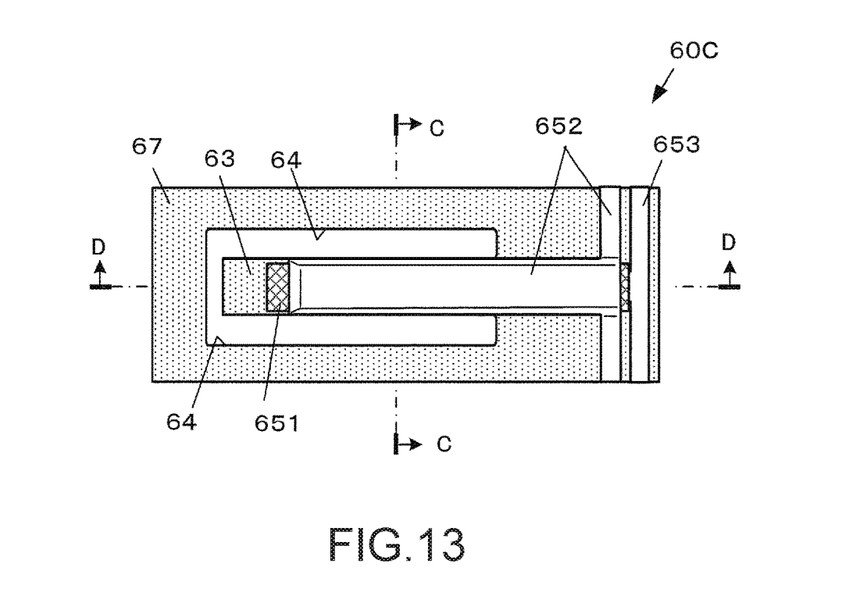
FIG. 13 is a top view showing a configuration example of a second piezoelectric element of a third embodiment.
Figure 14:
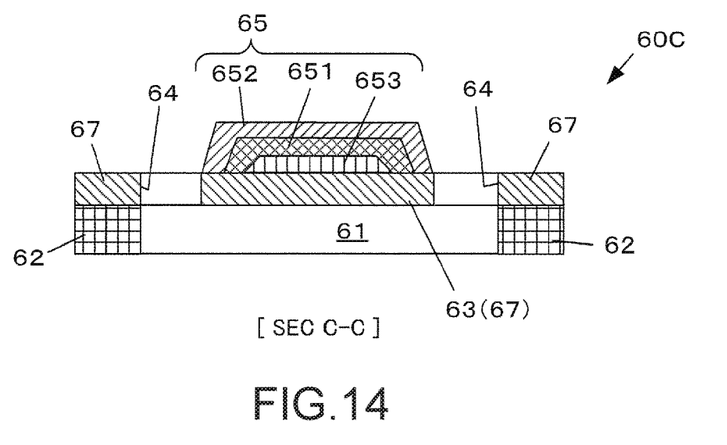
FIG. 14 is a sectional view taken along line C-C of FIG. 13.
Figure 15:
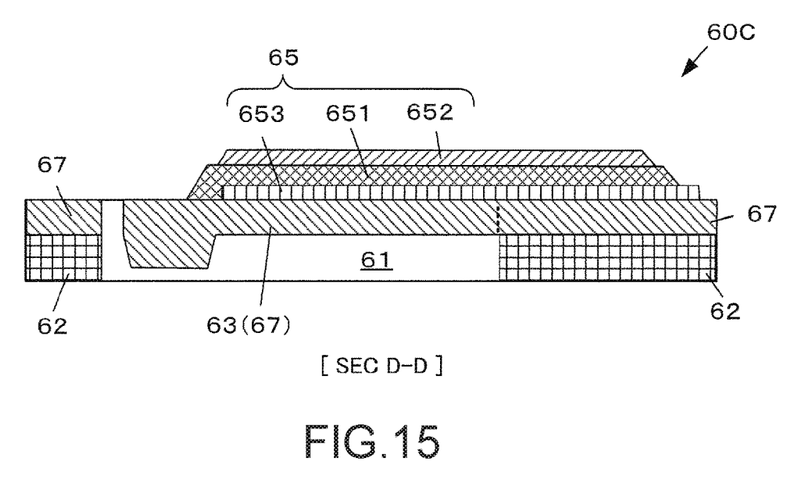
FIG. 15 is a sectional view taken along line D-D of FIG. 13.

FIG. 13 is a top view showing a configuration example of a second piezoelectric element 60C of the embodiment. FIG. 14 is a sectional view taken along line C-C of FIG. 13. FIG. 15 is a sectional view taken along line D-D of FIG. 13. In the second piezoelectric element 60C of the embodiment, a cantilever beam structure of a thin film in which the vibrating plate 63 is extended to the hollow portion 61 is formed.

The patterning of the silicon wafer 7 of the silicon layer 67 including the vibrating plate 63 is performed in the same manner as in the first embodiment or the second embodiment.

According to the embodiment, the same effects as in the first embodiment are obtained. The configuration described above is suitable for a case of using a piezoelectric element to which the invention is applied as an acceleration sensor, or a case of using the piezoelectric element as an energy harvester element.

MODIFICATION EXAMPLES

Hereinabove, the embodiments to which the invention is applied have been described, but adding, omission, and modification of the constituent elements can be suitably performed.

First Example

Figure 16:
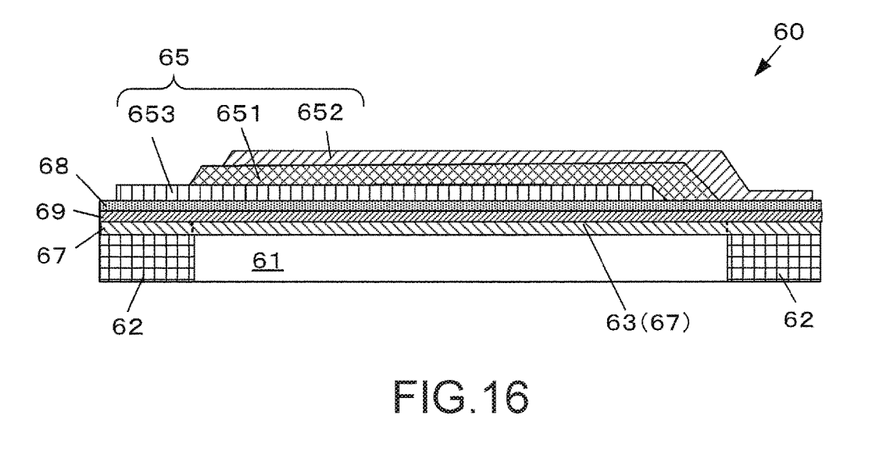
FIG. 16 is a sectional view showing a modification example of a configuration of the second piezoelectric element (first example).

For example, in the embodiments described above, the vibrating plate 63 has a single-layer structure of silicon, but as shown in a vibrating plate longitudinal direction sectional view of FIG. 16 (corresponding to FIG. 5), a multi-layer structure including a zirconia oxide layer 68 or a silicon dioxide layer 69 between the vibrating plate 63 and the power generation element unit 65 may be used.

Second Example

Figure 17:
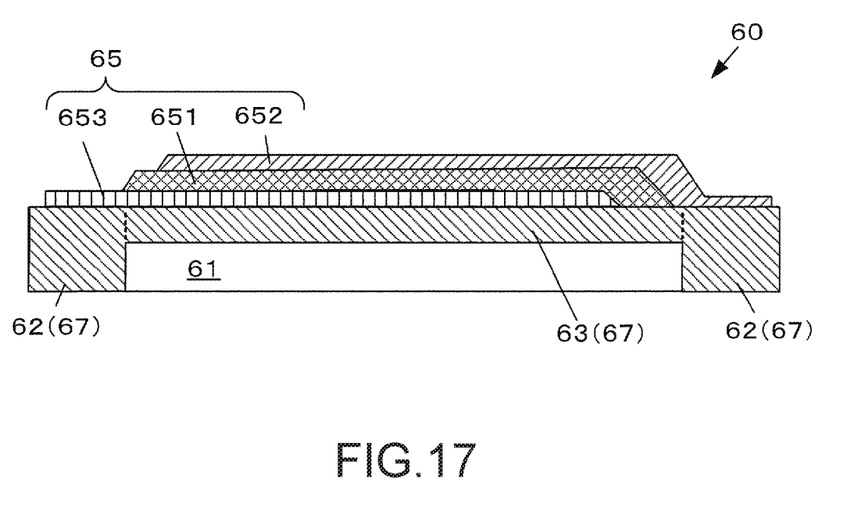
FIG. 17 is a sectional view showing a modification example of a configuration of the second piezoelectric element (second example).

In the embodiments described above, the support substrate 62 and the silicon layer 67 are separate materials, but as shown in a vibrating plate longitudinal direction sectional view of FIG. 17, the same material is used for the support substrate 62 and the silicon layer 67, and the hollow portion 61 may be prepared by etching or the like.

Third Example

Figure 18:
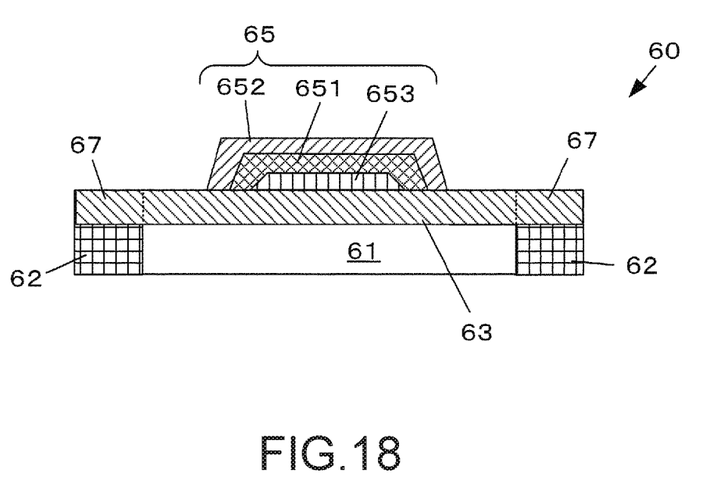
FIG. 18 is a sectional view showing a modification example of a configuration of the second piezoelectric element (third example).

In the embodiments described above, the slits 64 are provided around the vibrating plate 63, but as shown in the sectional view of FIG. 18 (corresponding to FIG. 4), the slits 64 may be omitted. For example, when the vibrating plate 63 has a rectangular shape in a top view, a support structure in which the four sides are supported by the support substrate 62 can be used. In this case, since the high expansion and contraction direction when an external force is received is set as the short direction of the vibrating plate 63 (piezoelectric body 651), the vibrating plate 63 may be prepared and laminated so that this direction is along the low Poisson's ratio orientation. The same can also be applied to the configurations of FIG. 16 and FIG. 17.

Fourth Example

In the embodiments described above, each ultrasonic transducer 46 includes the first piezoelectric element 50 for transmission and the second piezoelectric element 60 for reception, separately, but the second piezoelectric element 60 may also serve as a piezoelectric element for transmission and the first piezoelectric element 50 may not be used.

Fifth Example

In the embodiments described above, single crystal silicon is used as the material of the vibrating plate 63, but other materials may be used as long as they are materials capable of preparing a thin plate in the crystal orientation plane having anisotropy of a Poisson's ratio in a deviation angle direction. For example, a material such as other elements belong to the same carbon family (carbon group) of silicon such as gallium arsenide can be used.

Sixth Example

The first embodiment can also be applied to single crystal silicon of the plane orientation [010] and single crystal silicon of the plane orientation [100].

Figure 19:
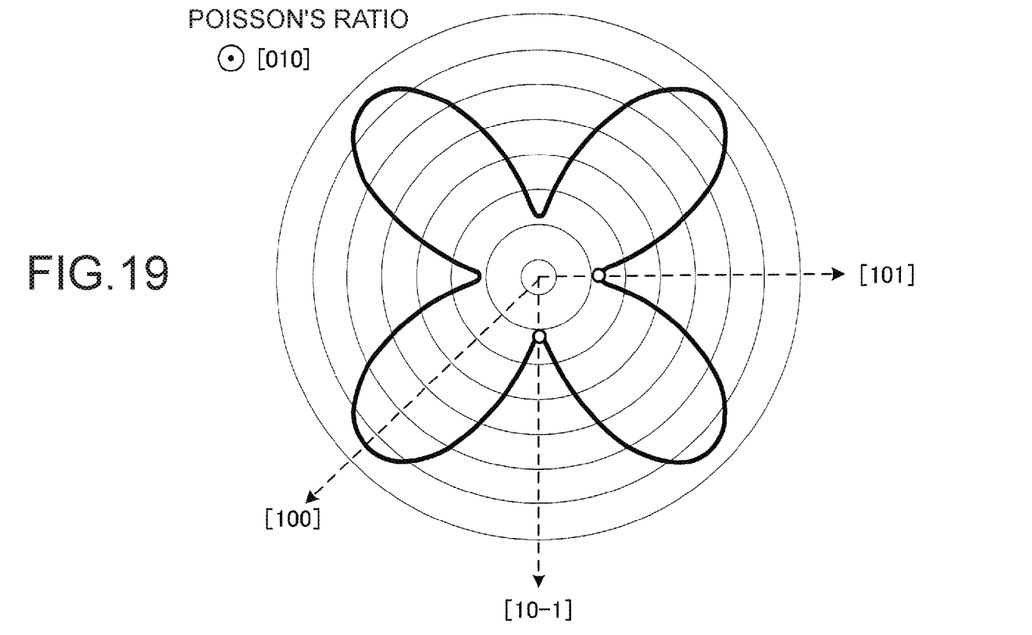
FIG. 19 is a graph showing an example of anisotropy of a Poisson's ratio of the [010] plane of single crystal silicon.

That is, the Poisson's ratio of the [010] plane of the single crystal silicon has anisotropy, as shown in FIG. 19. Accordingly, the material of the vibrating plate 63 may be cut out from the single crystal silicon of the plane orientation [010] so that the longitudinal direction becomes a direction along any of the plane orientation [101] and the plane orientation [10-1] where the Poisson's ratio locally decreases.

Figure 20:
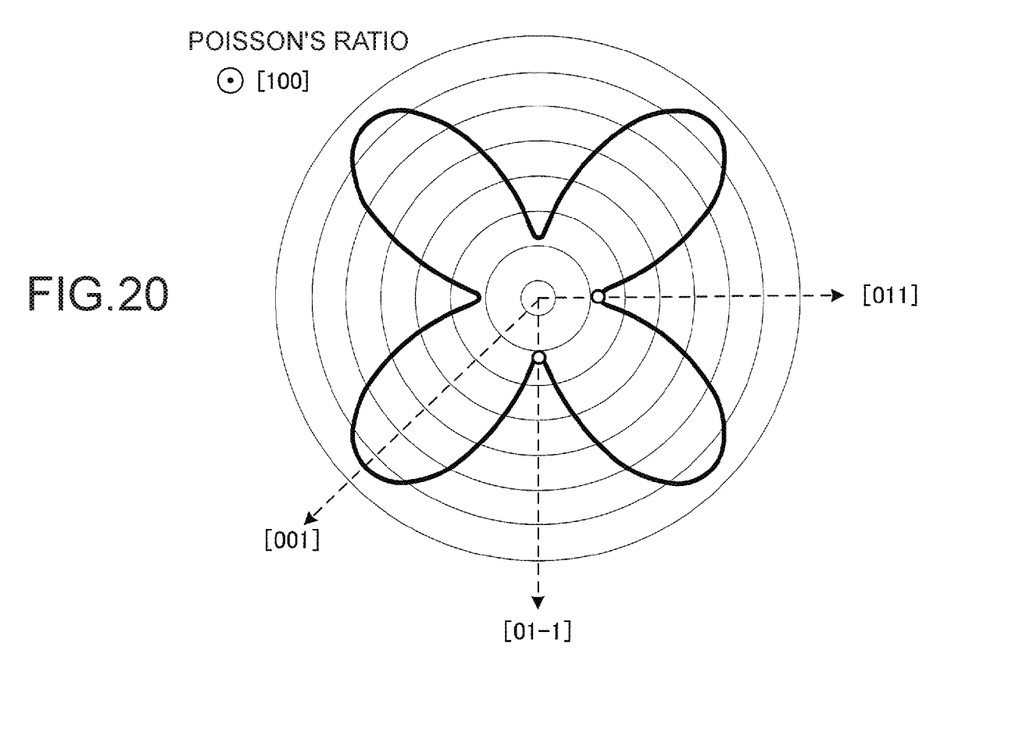
FIG. 20 is a graph showing an example of anisotropy of a Poisson's ratio of the [100] plane of single crystal silicon.

In the same manner as described above, the Poisson's ratio of the [100] plane of the single crystal silicon has anisotropy, as shown in FIG. 20. Accordingly, the material of the vibrating plate 63 may be cut out from the single crystal silicon of the plane orientation [100] so that the longitudinal direction becomes a direction along any of the plane orientation [011] and the plane orientation [01-1] where the Poisson's ratio locally decreases.

Seventh Example

The second embodiment can also be applied to single crystal silicon of the plane orientation [011] and single crystal silicon of the plane orientation [101].

Figure 21:
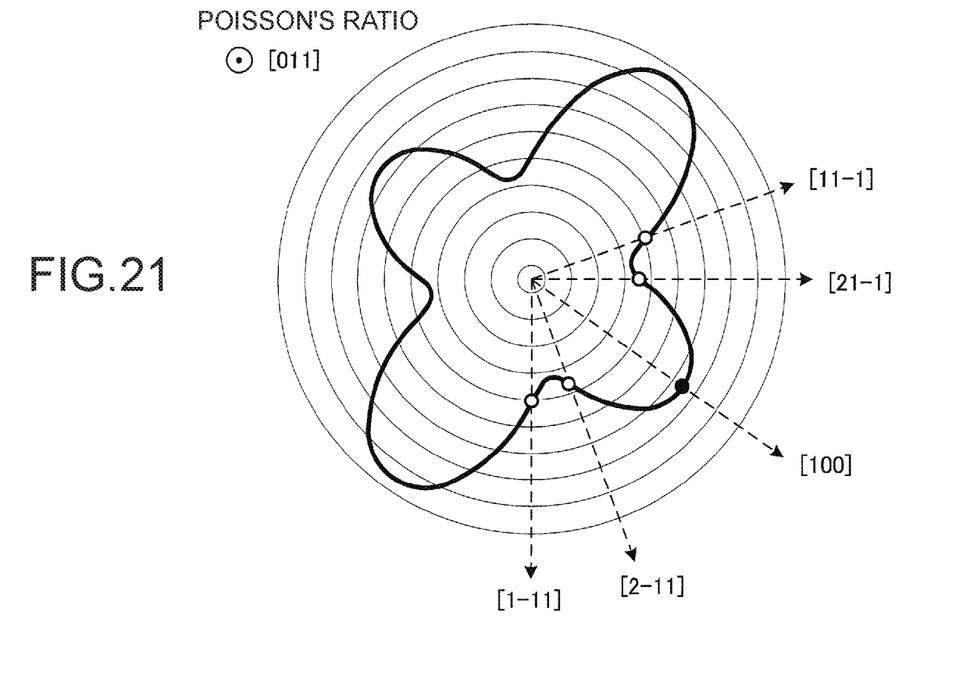
FIG. 21 is a graph showing an example of anisotropy of a Poisson's ratio of the [011] plane of single crystal silicon.

That is, the Poisson's ratio of the [011] plane of the single crystal silicon has anisotropy, as shown in FIG. 21. Accordingly, the material of the vibrating plate 63 may be cut out from the single crystal silicon of the plane orientation [011] so that the longitudinal direction becomes a direction along any of the plane orientation [11-1], the plane orientation [21-1], the plane orientation [2-11], the plane orientation [1-11] where the Poisson's ratio locally decreases.

Figure 22:
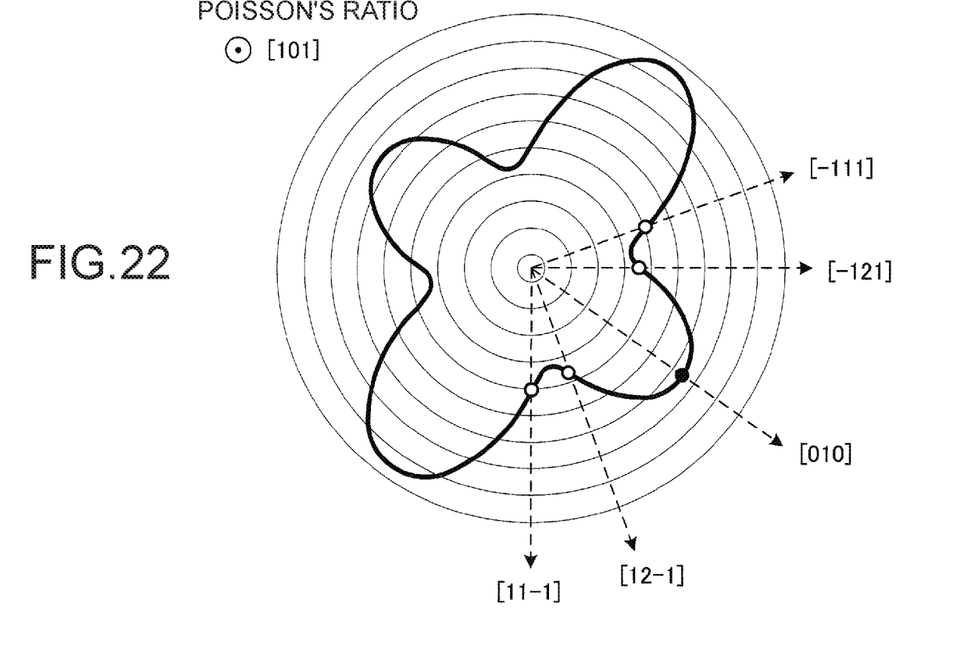
FIG. 22 is a graph showing an example of anisotropy of a Poisson's ratio of the [101] plane of single crystal silicon.

In the same manner as described above, the Poisson's ratio of the [101] plane of the single crystal silicon has anisotropy, as shown in FIG. 22. Accordingly, the material of the vibrating plate 63 may be cut out from the single crystal silicon of the plane orientation [101] so that the longitudinal direction becomes a direction along any of the plane orientation [-111], the plane orientation [-121], the plane orientation [12-1], and the plane orientation [11-1] where the Poisson's ratio locally decreases.

The entire disclosure of Japanese Patent Application No. 2015-215987 filed on Nov. 2, 2015 is expressly incorporated by reference herein.

What is claimed is:

1. A piezoelectric element comprising:
   a piezoelectric body; and
   a vibrating plate including single crystal silicon having anisotropy having orientation with a relatively high Poisson's ratio and orientation with a relatively low Poisson's ratio as a vibrating material,
   wherein the piezoelectric body and the vibrating plate are laminated on each other so that the orientation with the relatively low Poisson's ratio is in a direction along a high expansion and contraction direction among a direction where a degree of expansion and contraction caused according to a support structure of the piezoelectric body is relatively high and a direction where a degree thereof is relatively low.

2. The piezoelectric element according to claim 1, wherein plane orientation of the single crystal silicon is [001] and the orientation with the relatively low Poisson's ratio is [-110] or [110].

3. The piezoelectric element according to claim 1, wherein plane orientation of the single crystal silicon is [010] and the orientation with the relatively low Poisson's ratio is [101] or [10-1].

4. The piezoelectric element according to claim 1, wherein plane orientation of the single crystal silicon is [100] and the orientation with the relatively low Poisson's ratio is [011] or [01-1].

5. The piezoelectric element according to claim 1, wherein plane orientation of the single crystal silicon is [110] and the orientation with the relatively low Poisson's ratio is any one of [1-11], [1-12], [-112], and [-111].

6. The piezoelectric element according to claim 1, wherein plane orientation of the single crystal silicon is [011] and the orientation with the relatively low Poisson's ratio is any one of [11-1], [21-1], [2-11], and [1-11].

7. The piezoelectric element according to claim 1, wherein plane orientation of the single crystal silicon is [101] and the orientation with the relatively low Poisson's ratio is any one of [-111], [-121], [12-1], and [11-1].

8. An ultrasonic probe comprising the piezoelectric element according to claim 1 for reception of ultrasonic waves.

9. An ultrasonic probe comprising the piezoelectric element according to claim 2 for reception of ultrasonic waves.

10. An ultrasonic probe comprising the piezoelectric element according to claim 3 for reception of ultrasonic waves.

11. An ultrasonic probe comprising the piezoelectric element according to claim 4 for reception of ultrasonic waves.

12. An ultrasonic probe comprising the piezoelectric element according to claim 5 for reception of ultrasonic waves.

13. An ultrasonic probe comprising the piezoelectric element according to claim 6 for reception of ultrasonic waves.

14. An ultrasonic measurement device comprising the ultrasonic probe according to claim 8.

15. An ultrasonic measurement device comprising the ultrasonic probe according to claim 9.

16. An ultrasonic measurement device comprising the ultrasonic probe according to claim 10.

17. An ultrasonic measurement device comprising the ultrasonic probe according to claim 11.

18. An ultrasonic measurement device comprising the ultrasonic probe according to claim 12.

19. An ultrasonic measurement device comprising the ultrasonic probe according to claim 13.

\* \* \* \* \*